(12) United States Patent
Hanson et al.

(10) Patent No.: US 9,149,627 B2
(45) Date of Patent: Oct. 6, 2015

(54) KITS AND METHODS FOR IMPLANTING AN IMPLANTABLE LEAD EXTENSION

(71) Applicant: Medtronic, Inc., Minneapolis, MN (US)

(72) Inventors: Scott M. Hanson, Savage, MN (US); Evan M. Gustafson, Golden Valley, MN (US); Joseph P. Ricci, Ham Lake, MN (US); Adam J. Rivard, Blaine, MN (US); Joshua D. Trevorrow, Minneapolis, MN (US); Chad C. Whiterabbit, Mahtomedi, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 0 days.

(21) Appl. No.: 14/179,668

(22) Filed: Feb. 13, 2014

(65) Prior Publication Data

US 2014/0277315 A1    Sep. 18, 2014

Related U.S. Application Data

(60) Provisional application No. 61/781,622, filed on Mar. 14, 2013.

(51) Int. Cl.
*A61N 1/00* (2006.01)
*A61N 1/05* (2006.01)
*A61N 1/375* (2006.01)
*A61N 1/04* (2006.01)

(52) U.S. Cl.
CPC ............... *A61N 1/05* (2013.01); *A61N 1/0488* (2013.01); *A61N 1/375* (2013.01)

(58) Field of Classification Search
USPC .......................................... 607/116
See application file for complete search history.

(56) References Cited

U.S. PATENT DOCUMENTS

| | | |
|---|---|---|
| 5,782,841 A | 7/1998 | Ritz et al. |
| 6,605,094 B1 | 8/2003 | Mann et al. |
| 8,355,787 B2 | 1/2013 | Barker |
| 2008/0132969 A1* | 6/2008 | Bennett et al. ............... 607/41 |
| 2009/0030426 A1 | 1/2009 | Zinn et al. |
| 2011/0208265 A1* | 8/2011 | Erickson et al. ............ 607/46 |
| 2012/0016377 A1 | 1/2012 | Geroy |
| 2012/0059321 A1 | 3/2012 | Hammond et al. |
| 2012/0083794 A1 | 4/2012 | Martin et al. |
| 2012/0191106 A1 | 7/2012 | Ko et al. |
| 2014/0228643 A1* | 8/2014 | Possover ................... 600/160 |

* cited by examiner

*Primary Examiner* — Robert N Wieland
(74) *Attorney, Agent, or Firm* — Withers & Keys, LLC

(57) ABSTRACT

Kits provide management of implantable lead extensions being implanted by providing a kit body with features that retain the extension in a configuration, with amounts being removed as needed during the implantation procedure. The kit can be present within a sterile field, and the kit body features may be arranged so that a length of a path that the extension forms is approximately equal to a length of the extension needed for the tunnel. The kit body may include features that allow the connectors of the extension as well as implantation tools to be retained within the kit body while being easily accessed when needed during the procedure. The kit may be coupled to the patient during the trial period, as the extension may have an implanted distal connector while having a proximal connector coupled to an external stimulator and while being retained on the kit body.

33 Claims, 8 Drawing Sheets

KITS AND METHODS FOR IMPLANTING AN IMPLANTABLE LEAD EXTENSION

TECHNICAL FIELD

Embodiments relate to the implantation of implantable lead extensions. More particularly, embodiments relate to kits and related methods used when implanting an implantable lead extension.

BACKGROUND

When a patient is a candidate for stimulation therapy such as sacral nerve stimulation or spinal cord stimulation therapy to treat incontinence, chronic pain, or related conditions, it is often desirable to conduct a trial period of stimulation. This trial period allows an external stimulator to be used so that the patient is not required to undergo a full stimulation device implantation procedure. If the trial is successful, then an implantable stimulator is fully implanted into the patient.

When implanting the trial system, an implantable medical lead is implanted with a distal end being routed to the stimulation site. An implantable lead extension is typically then routed subcutaneously from the location of the proximal end of the implanted medical lead to an exit site nearby the location where the external device will be mounted to the patient. An external lead is then used to interconnect the exposed proximal end of the implantable lead extension to the external device.

One issue with the external lead is that it requires a step of connecting the external device and to the lead extension. While this allows the lead extension to be shorter, and thus less burdensome during implantation and during the trial period, the external lead itself introduces the burden of having to install it and then have it be present during trialing. Thus, the external lead has two external connections, and both must be maintained during the trial period.

In addition to the burdens of the external lead, the implantation procedure has additional burdens related to accessing the tools needed to complete the implantation procedure. A nurse within a non-sterile field provides the packaging of the tools. A sterile nurse must then access the tools from the packaging and place the tools on a surgical tray within the sterile field. Meanwhile, the packaging is discarded. These steps add to the time and inefficiencies of the implantation procedure.

SUMMARY

Embodiments address issues such as these and others by providing a kit that has a body containing the extension and the tools for implanting the extension, where the kit can enter the sterile field and be used during the implantation procedure and even during the trial period. During the implantation procedure, the kit may be clipped to the surgical drape or otherwise secured nearby the incision sites and someone in the sterile field can access the extension and the tools as needed. The length of implantable lead extension needed at any time during the implantation procedure can be removed from the body while the body continues to retain the remaining length of implantable lead extension. The body of the kit may provide additional aspects such as being made of a material and shape that allows for direct attachment of the body to the patient. In that case, any excess amount of implantable lead extension remains organized on the body and out of the way during the trial period so as to not burden the patient. The body of the kit may also provide a mounting feature for the connectors on the implantable lead extension and mounting features for the tools that are used during the implantation procedure such as a tunneling tip and a pull-through tip.

Embodiments provide a kit that includes a body including features and an implantable medical lead extension attached to the body in a configuration defined by the features of the body. The implantable medical lead extension in the configuration includes a distal end connector having a bore for receiving a proximal end of an implantable medical lead and a proximal end connector having a main body with a pluggable physical connection framework for connecting to a stimulation device.

Embodiments provide a method of implanting an implantable lead extension that involves providing a kit comprising a body and the implantable medical lead extension attached to the body. The implantable medical lead extension includes a proximal connector and a distal connector. The method further involves removing from the body a portion of the implantable medical lead extension having a length that is adequate to extend through a subcutaneous tunnel present in a patient such that the implantable medical lead extension is in a partially removed configuration on the body.

Embodiments provide method of implanting an implantable lead extension that involves providing a kit comprising a body and the implantable medical lead extension attached to the body. The implantable medical lead extension includes a proximal connector and a distal connector. The method further involves introducing the kit into a sterile field where a patient is located and removing from the body at least a portion of the medical lead extension. Additionally, the method involves positioning the portion of the implantable medical lead extension within a subcutaneous tunnel within the patient.

Embodiments provide an implantable medical lead extension that includes an elongated portion containing electrical conductors. The extension further includes a distal end connector on a distal end of the elongated portion, with the distal end connector having a bore for receiving a proximal end of an implantable medical lead. The bore contains electrical connectors that are connected to corresponding electrical conductors from the elongated portion. The extension also includes a proximal end connector on a proximal end of the elongated portion, with the proximal end connector having a main body with a pluggable physical connection framework for connecting to a stimulation device. The proximal end connector has electrical connectors that are connected to corresponding electrical conductors from the elongated portion.

DETAILED DESCRIPTION

Embodiments provide methods and kits for implanting an implantable lead extension. The kits are introduced into the sterile field to condense the amount of steps being followed during implantation. An extension that may be included in the kit extends from the proximal end of the implantable lead to the external stimulator. The kit accounts for excessive length of the implantable lead extension during the implantation procedure as well as during the trial period for some embodiments. Furthermore, some embodiments of the kits allow for tools such as tunneling tips and pull-through tips for tunneling rods to be stored within the kit while in the sterile field until time for use during the implantation procedure thereby eliminating the use of a surgical tray for these items of the kit.

Figure 1:
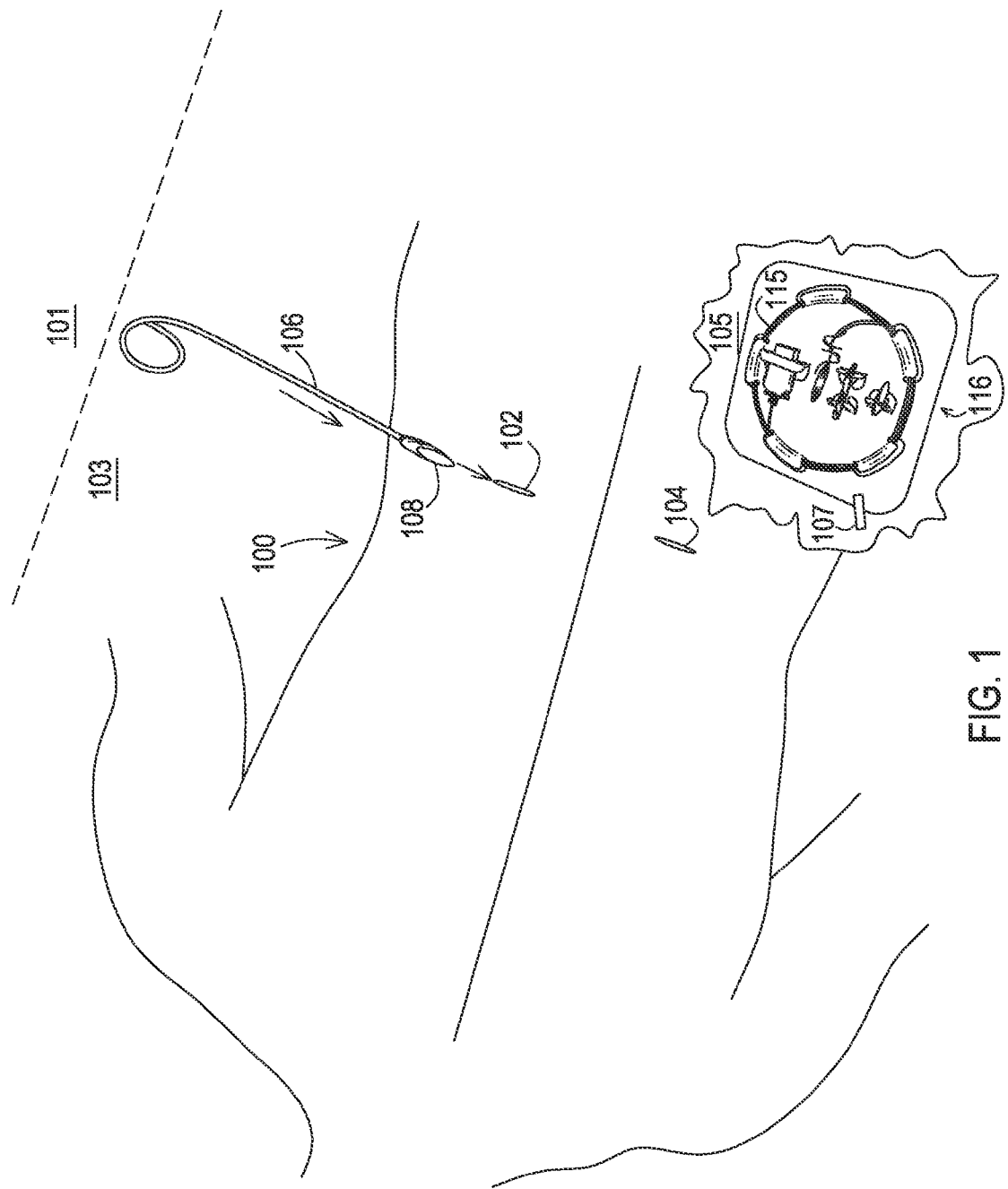
FIG. 1 shows a first stage of an implantation procedure where a tunnel is being created using a tunneling tip mounted to a tunneling rod.

FIG. 1 shows a first stage of an implantation procedure within a typical operating environment for the various embodiments where a non-sterile field 101 and a sterile field 103 are present as in a typical operating room. Here, a patient 100 is within the sterile field 103, and there are two surgical incisions 102, 104 made in the patient 100. Incision 102 is in proximity to the proximal end of the implantable lead, which may have already been routed within the patient 100 to the internal stimulation site. Incision 104 is in proximity to the intended mounting location of the external stimulator.

Figure 4:
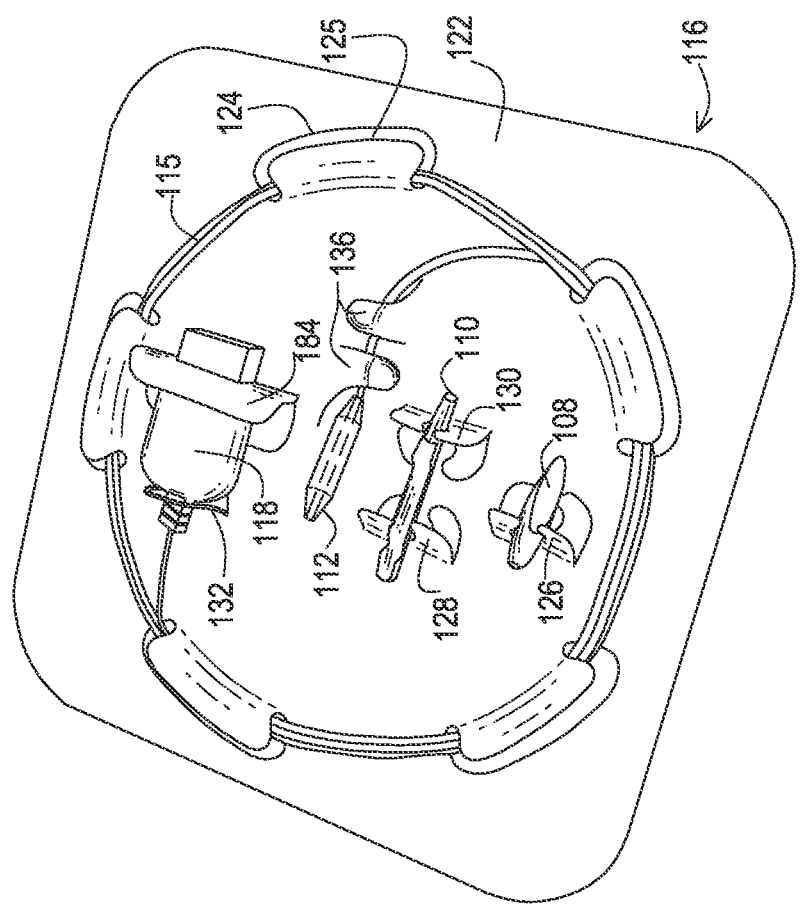
FIG. 4 shows a first example of a kit for implanting an implantable lead extension where a kit body is a sheet.
Figure 5:
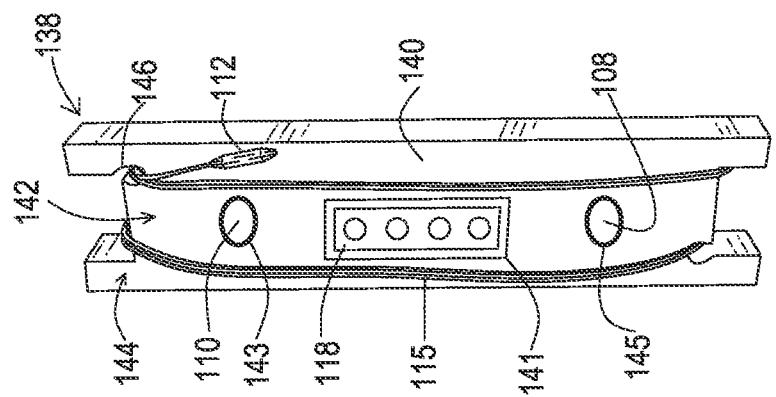
FIG. 5 shows a second example of a kit for implanting an implantable lead extension where a kit body is H-shaped.
Figure 6:
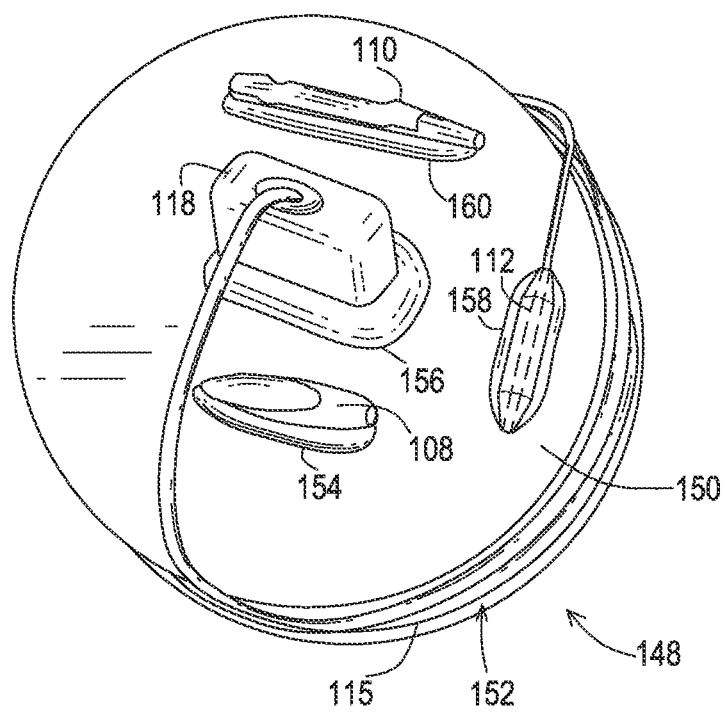
FIG. 6 shows a third example of a kit for implanting an implantable lead extension where a kit body is a disc.

A kit, such as the kit 116 of FIG. 4, the kit 138 of FIG. 5, or the kit 148 of FIG. 6 is present within the sterile field 103. For instance, the kit 116 may be attached to the surgical drape 105 with a clip 107 as shown in FIG. 1. Note that the kit 116 is not necessarily to scale in these figures and can be relatively small, on the order of a 4 inch by 4 inch square in the case of kit 116 of FIG. 4. The kit 116 includes a tunneling tip 108, and this tunneling tip 108 may be mounted within the kit where it is stored until needed by the surgeon and is easily accessed from the kit 116 at the appropriate time. The tunneling tip 108 is installed onto an end of a tunneling rod 106 that is manipulated by the surgeon. The tunneling tip 108 may attach to the end of the tunneling rod 106 in various ways, such as by having an end that is threaded onto matching threads present on the end of the tunneling tip 108.

The tunneling tip 108 is then inserted through the incision 102 and is forced subcutaneously by the tunneling rod 106 and by skillful manipulation from the surgeon until exiting through the incision 104. This effectively creates a tunnel through fatty tissue between the incision 102 and the incision 104.

Figure 2:
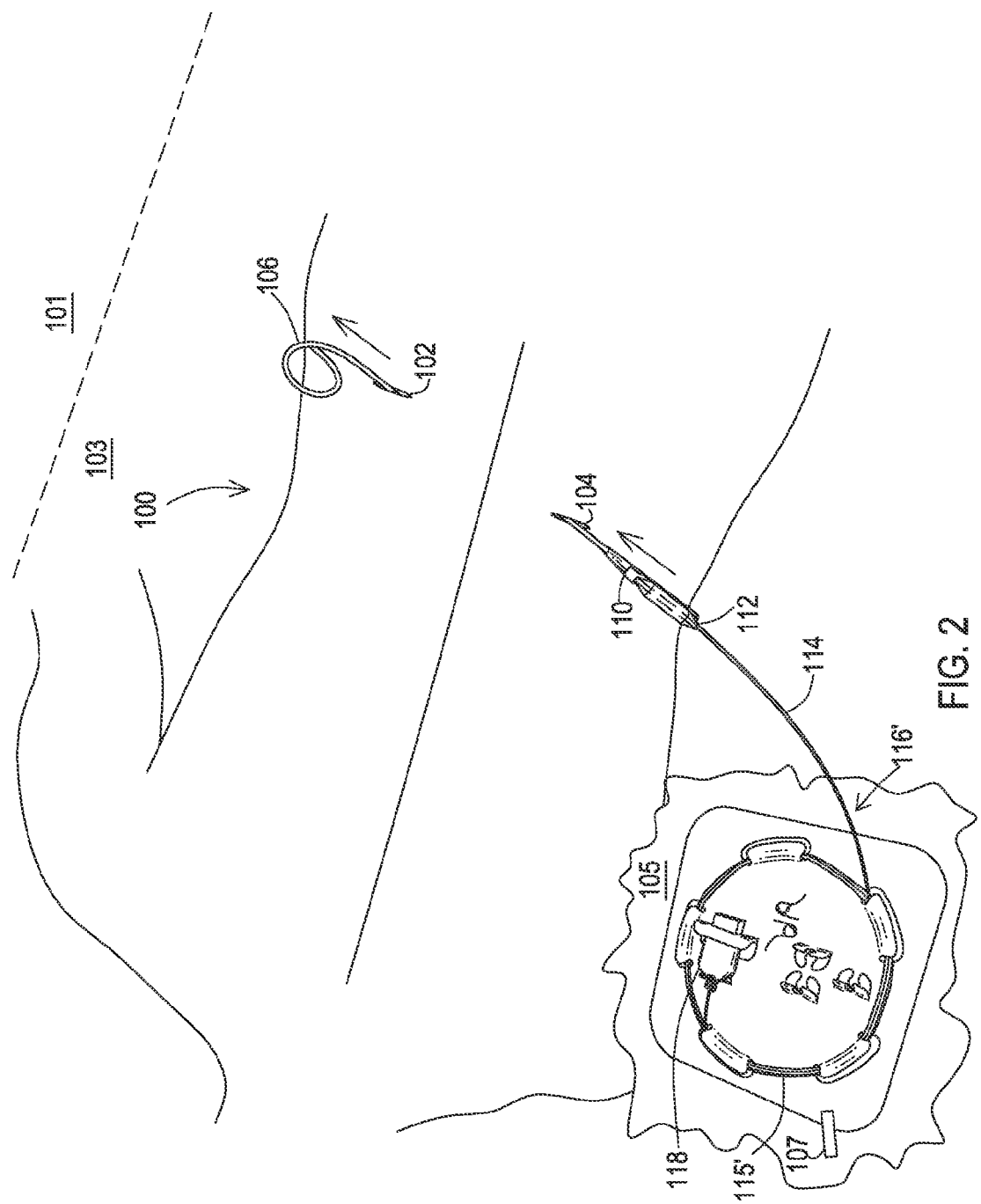
FIG. 2 shows a second stage of the implantation procedure where an implantable lead extension is pulled through the tunnel using a pull-through tip that is mounted to the tunneling rod.

As shown in FIG. 2, the tunneling tip 108 is removed while a pull-through tip 110 is taken from the kit 116 and installed on the end of the tunneling rod 106. The pull-through tip 110 may be of various forms such as a carrier that a distal end connector 112 of the implantable lead extension may be positioned within. Other examples of the pull-through tip 110 include a tip that is insertable within the distal end connector 112.

At this stage of the implantation procedure, the surgeon takes the kit 116 of FIG. 4, the kit 138 of FIG. 5, or the kit 148 of FIG. 6 and obtains an amount of the implantable lead extension starting at the distal end connector 112 that is necessary to extend between the incisions 102 and 104. The kits 116, 138, and 148 each retain the implantable lead extension 115 in an organized manner, for instance a spool, to effectively manage the extension cable length. This reduces the cumbersome nature of having an extension cable of significant length, on the order of 40 inches in some examples.

The removed portion 114 is then pulled through the tunnel between the incisions 102 and 104 by pulling the tunneling rod 106 back through the tunnel. Meanwhile, the retained portion 115' of the implantable lead extension remains with the kit 116'. While FIG. 2 shows this stage of the implantation procedure utilizing the kit 116' which corresponds to the kit 116 of FIG. 4, it will be appreciated that this implantation procedure may alternatively utilize the kit 138 of FIG. 5, the kit 148 of FIG. 6, or other styles of kits not shown that retain the implantable lead extension 115 and/or tools during the stages of the procedure. Other applicable styles of the kit may utilize other manners of retaining the extension 115, such as arranging the extension 115 into a sinusoidal shape.

Figure 3:
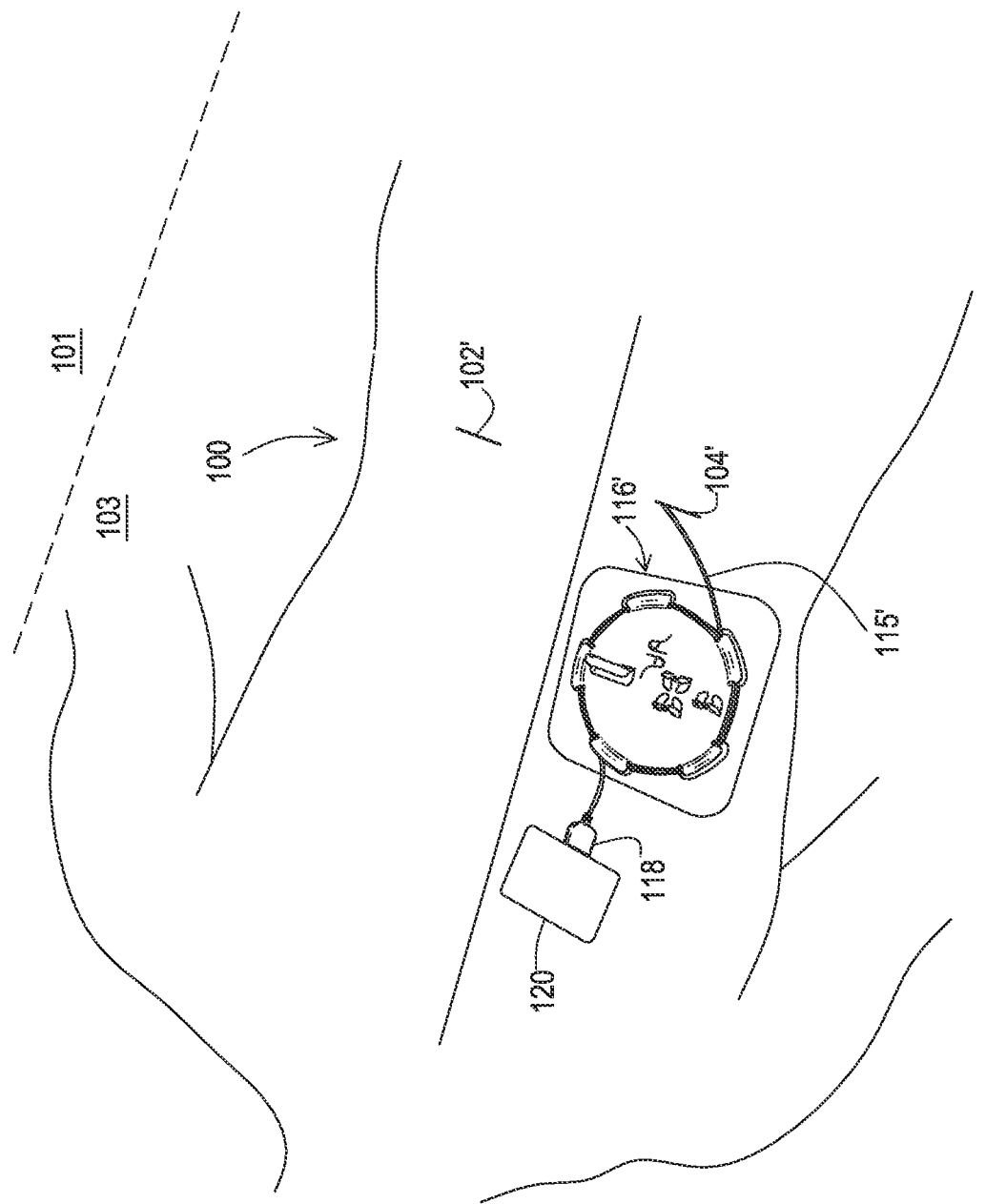
FIG. 3 shows a third state of the implantation procedure where the implantable lead extension is connected to an external stimulator while in a spooled configuration on a kit body.

A subsequent stage of the implantation procedure is shown in FIG. 3. Here, the incisions 102', 104' are closed with the implantable lead extension portion 114 exiting the closed incision 104' while the retained portion 115' remains with the kit 116'. The distal end connector 112 is no longer visible as it has been connected to the proximal end of the implanted lead and stored subcutaneously beneath the closed incision 102'. A proximal connector 118 of the implantable lead extension has been connected to an external stimulator 120 by being removed from the kit 116' with the proximal end of the implantable lead extension also being partially removed as needed.

In this example, the kit 116' is attached to the patient 100 in proximity to the attachment of the external stimulator 120 to the patient 100. The kit 116' may be attached in various ways, such as by being taped or glued to the skin of the patient 100 such as by adhesive backed tape on the underside of the kit 116'. The kit 116' remains with the patient during the trial period and continues to manage the excess length of the implantable medical lead by retaining the portion 115' in the organized configuration. Once the trial period ends, the kit 116' is removed from the skin of the patient and the external stimulator 120 and the implantable lead extension 115 are removed. In the case of a successful trial, these items are replaced by a fully implanted stimulator.

With reference to FIG. 4, the kit 116 of this example includes a kit body 122 that may be constructed of a relatively thin, flexible, biocompatible material that allows for attachment to the patient 100. Examples of such materials include high density polyethylene, Polypropylene, Polyethylene terephthalate (PET), Linear low-density polyethylene (LL-DPE), Reinforced paper, Tyvek®, Spun bound Polyolefin, Silicone, and the like. The kit 116 may be provided in a sterilized manner within packaging such as a Tyvek® polymer pouch such that the entire kit can be taken into the sterile field 103 upon being removed from the pouch.

To manage the implantable lead extension 115, the kit body 122 of this example includes cut-outs 124 and resulting retention flaps 125. These features are shaped and positioned so as to create a spool that has a somewhat circular path for the implantable lead extension 115 with the flaps 125 at the cutouts 124 retaining the implantable lead extension 115. As discussed above, over manners of organizing the extension 115 are also applicable, such as a sinusoidal path rather than a circular path. The path created by the cutouts 124 and flaps 125 may be chosen so that the length of the path is approximately equal to the length of implantable extension lead that is needed to pass through the tunnel between the incision sites 102, 104 for the majority of patients 100. In the example shown, where the path is circular, the circumference of the path may correspond to the length needed for tunneling. This allows the surgeon to quickly obtain the removed portion 114 of FIG. 2 with an adequate length without having an unnecessary amount removed by unwrapping one turn of the implantable lead extension 115 from the body 122. For instance, a length of the path of approximately 13 inches may provide an adequate length of removed portion 114 for many circumstances. Or, the adequate length of lead extension could be left free from the body 140 as packaged, eliminating the need to unspool any length of lead extension to pass through the tunnel between incision sites 102, 104 for the majority of patients 100.

The kit body 122 also includes several flaps that may be used to retain other items. For example, flap 126 retains the tunneling tip 108 while flaps 128, 130 retain the pull-through tip 110 such as a carrier or an insertable pin. These flaps may be formed by being trimmed and then rotated upward from the sheet 122. Flaps 132, 134 retain the proximal connector 118 while flaps 136 capture the distal end of the implantable lead extension 115 so as to retain the distal connector 112. The kit 116 is thereby made compact while each of the items remains easily accessible. As an alternative to the configuration shown in FIG. 4, the distal end 112 can be preloaded into pull-through tip 110 and rest in the recess 160.

With reference to FIG. 5, the kit 138 of this example includes a kit body 140 that may be constructed of a rigid material that allows for an H-shape to be achieved. Examples of such materials include Delrin®, Polyethylene (PE), Polycarbonates (PC), Silicone, Polyether Urethane. The kit 138 may also be provided in a sterilized manner within packaging such as a Tyvek® polymer pouch. Thus, this kit 138 may be introduced into the sterile field 103 upon being unpackaged. Furthermore, this kit may be coupled to the patient during the trial period, such as by being tied, wrapped, hooked to a belt, and so forth.

To manage the implantable lead extension 115, the kit body 140 of this example includes the legs 144 of the H-shape so as to create a center section 142 that forms a spool for the implantable lead extension 115. Grooves 146, notches, or other features may be present to further contain the turns of the implantable lead extension 115 and to prevent unintended unwinding. The path of the spool created by the H-shape may also be chosen so that the length of the path is approximately equal to the length of implantable extension lead that is needed to pass through the tunnel between the incision sites 102, 104 for the majority of patients 100. This also allows the surgeon to quickly obtain the removed portion 114 with an adequate length without having an unnecessary amount removed by unwrapping one turn of the implantable lead extension 115 from the body 140. Or, the adequate length of lead extension could be left free from the body 140 as packaged, eliminating the need to unspool any length of lead extension to pass through the tunnel between incision sites 102, 104 for the majority of patients 100.

The kit body 140 also includes several apertures that may be used to retain other items. For example, aperture 145 allows the tunneling tip 108 to be inserted for an interference fit but with easy removal by grasping and pull free of the aperture 145. Aperture 143 allows the pull-through tip 110 to be inserted for an interference fit but with easy removal. Aperture 141 receives the proximal connector 118 to provide an interference fit with easy removal. The kit 138 is thereby made compact while each of the items remains easily accessible. Alternatively to the example shown in FIG. 5, the distal tip 112 of the extension may be preloaded into the pull-through tip 110 and loaded into aperture 143.

With reference to FIG. 6, the kit 148 of this example includes a kit body 150 that may be constructed of a rigid material that allows for a disc to be achieved. Examples of such materials include PC, Silicone, PEEK, PE, high density PE, LLDPE, and Delrin®. The kit 148 may also be provided in a sterilized manner within packaging such as a Tyvek® polymer pouch. Thus, this kit 148 may be introduced into the sterile field 103 upon being unpackaged. Furthermore, this kit may also be coupled to the patient during the trial period, such as by being tied, wrapped, hooked to a belt, and so forth.

To manage the implantable lead extension 115, the kit body 150 of this example has a depth that allows for an outer groove 152 to be formed that provides a spool to receive and maintain the implantable lead extension 115 in an organized configuration. The circumference of the spool created by the groove 152 may also be chosen to be approximately equal to the length of implantable extension lead that is needed to pass through the tunnel between the incision sites 102, 104 for the majority of patients 100. This also allows the surgeon to quickly obtain the removed portion 114 with an adequate length without having an unnecessary amount removed by unwrapping one turn of the implantable lead extension 115 from the body 150. Or, the adequate length of lead extension could be left free from the body 140 as packaged, eliminating the need to unspool any length of lead extension to pass through the tunnel between incision sites 102, 104 for the majority of patients 100.

The kit body 150 of this example also includes several recesses present within the depth of the disc body 150 that may be used to retain other items. For example, recess 154 allows the tunneling tip 108 to be inserted for an interference fit but with easy removal by grasping and pulling free of the recess 154. Recess 160 allows the pull-through tip 110 to be inserted for an interference fit but with easy removal. Recess 156 receives the proximal connector 118 to provide an interference fit with easy removal. Recess 158 receives the distal connector 112 to provide an interference fit with easy removal. The kit 148 is thereby made compact while each of the items remains easily accessible. Alternatively to the example shown in FIG. 6, the distal end 112 of the extension can be preloaded into pull-through tip 110 and rest in the recess 160.

Figure 7:
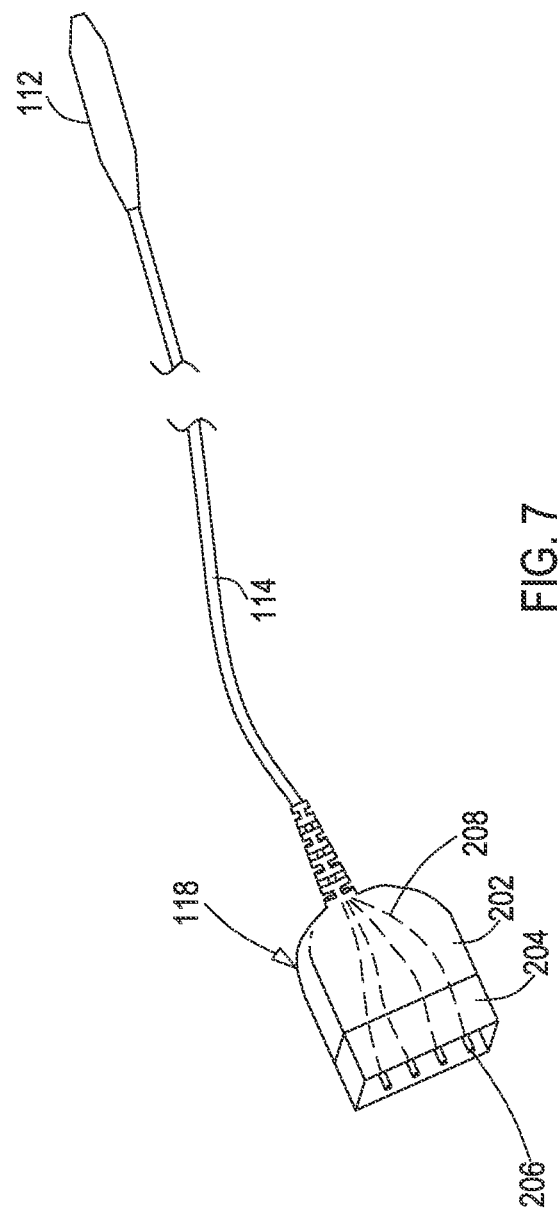
FIG. 7 shows an example of the implantable medical lead extension.

FIG. 7 shows the lead extension in more detail. The lead extension includes the elongated body that forms the removed portion 114 that is pulled through the tunnel. The elongated body terminates in the distal connector 112 that includes a body 210 defining a bore 212 for receiving the proximal end of the implantable lead.

Because the lead extension of this example extends from the proximal end of the implantable lead to the external device 120 shown in FIG. 3, the lead extension includes the proximal connector 118 which is designed to plug into the external device. One example of the proximal connector 118 is the model LX40-20P provided by the Hirose Electric Company, LTD. The proximal connector 118 includes a main connector body 202 that is a rigid structure that houses the conductors 208 that provide the electrical pathway through the extension to the distal connector 112. The main connector body 202 can be easily grasped by the physician to plug or unplug the connector 118 relative to the port of the external device 120.

The proximal connector 118 provides electrical connectors 206 that make contact with electrical connectors in the port of the external device 120. As can be seen in FIG. 7, these electrical connectors 206 are oriented perpendicularly from the elongation of the extension such as the removed portion 114. In this example, a physical connection framework 204 extends from the main housing 202 and houses the exposed electrical connectors 206. The physical connection framework 204 mechanically engages the port of the external device 120 to maintain the connection during the trial period.

Figure 8:
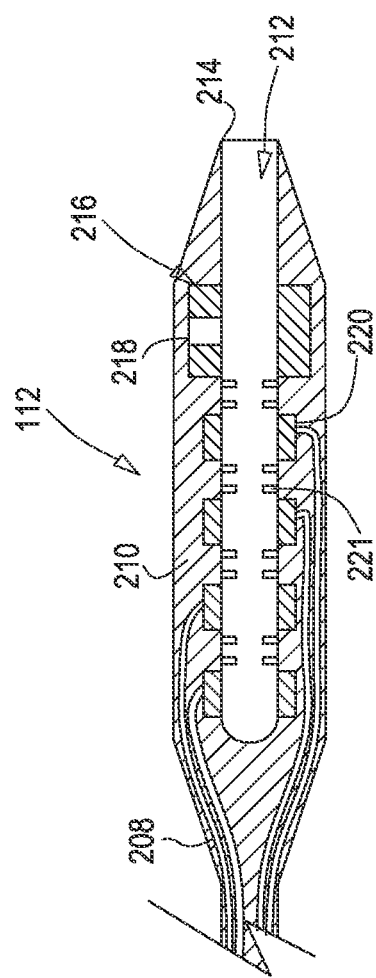
FIG. 8 shows an example of a distal connector of the extension shown in cross-section.

FIG. 8 shows an example of a distal connector 112 in a longitudinal cross-section. The distal connector 112 includes the body 210 which may be constructed as an assembly of components, such as a peek body surrounded by liquid silicone rubber. The body 210 contains electrical connectors 220, separated by seals 221, that surround a bore 212 within which the proximal end of the implanted lead is positioned upon being inserted longitudinally through an opening 214. The electrical connectors 220 contact the electrical connectors on the proximal end of the implanted lead. Electrical conductors such as filars 208 extend into the body 210 and are routed to corresponding electrical connectors 220. In this example, each electrical connector 206 of the proximal connector 118 has electrical continuity with a corresponding electrical connector 220 within the distal connector 112. The electrical connectors may be of various types. One example is the Bal Seal® canted coil spring connector.

In this example, the distal connector 112 also includes a set screw body 216 defining a set screw bore 218. A set screw can be tightened within the bore 218 to engage a clink or other structure of the implantable lead to hold the lead in a fixed position within the bore 212. Other retention structures that fix the position of the implanted lead within the bore 212 may also be applicable within the distal connector 112.

While embodiments have been particularly shown and described, it will be understood by those skilled in the art that various other changes in the form and details may be made therein without departing from the spirit and scope of the invention.

What is claimed is:

1. A kit, comprising:
   a body having features; and
   an implantable medical lead extension attached to the body by being wound around the features of the body, with the implantable medical lead extension in the configuration including a distal end connector having a bore for receiving a proximal end of an implantable medical lead and a proximal end connector having a main body with a pluggable physical connection framework for connecting to a stimulation device.

2. The kit of claim 1, further comprising a tool for implanting the implantable lead extension that is attached to the body.

3. The kit of claim 2, wherein the body is a sheet and the features comprise a plurality of cut-outs, the implantable medical lead extension being passed through the cut-outs to form the configuration.

4. The kit of claim 3, wherein the cut-outs are positioned on the sheet such that a circumference of the configuration corresponds to a length of the implantable medical lead extension needed for tunneling to a lead connection site from an entry site.

5. The kit of claim 4, wherein the sheet comprises a plurality of flaps, the kit further comprising a tool for implanting the implantable lead extension that is attached to at least one flap of the plurality.

6. The kit of claim 5, wherein the proximal end connector and the distal end connector are attached to flaps of the plurality.

7. The kit of claim 6, wherein the body is constructed of a flexible material.

8. The kit of claim 6, wherein the body comprises high density polyethylene.

9. The kit of claim 1, wherein the features of the body create an H-shape with the implantable medical lead being wrapped about a central portion of the H-shaped body.

10. The kit of claim 9, wherein the body defines an aperture, the kit further comprising a tool for implanting the implantable lead extension that is positioned within the aperture of the body.

11. The kit of claim 10, wherein the proximal end connector and the distal end connector are positioned within corresponding apertures of the body.

12. The kit of claim 1, wherein the body comprises a disc and wherein the features provide an outer groove about a circumference of the disc and wherein the implantable medical lead extension is positioned about the groove.

13. The kit of claim 12, wherein the disc defines a recess, the kit further comprising a tool for implanting the implantable lead extension that is positioned within the corresponding recess of the body.

14. The kit of claim 13, wherein the proximal end connector and the distal end connector are positioned within corresponding recesses of the body.

15. A method of implanting an implantable lead extension, comprising:
   providing a kit comprising a body and the implantable medical lead extension attached to the body, the implantable medical lead extension including a proximal connector and a distal connector; and
   removing from the body a portion of the implantable medical lead extension having a length that is adequate to extend through a subcutaneous tunnel present in a patient such that the implantable medical lead extension is in a partially removed configuration on the body.

16. The method of claim 15, further comprising attaching the body having the implantable medical lead extension in the partially removed configuration to an external location on the patient.

17. The method of claim 16, wherein the kit further comprises a tunneling tip attached to the body, the method further comprising removing the tunneling tip from the body and utilizing the tunneling tip to form the subcutaneous tunnel.

18. The method of claim 17, wherein the body comprises a sheet having flaps and wherein the tunneling tip is attached between two flaps.

19. The method of claim 17, wherein the body comprises an aperture and wherein the tunneling tip is attached within the aperture.

20. The method of claim 17, wherein the body comprises a recess and wherein the tunneling tip is attached to the recess.

21. The method of claim 20 wherein the kit further comprises a pull-through tip attached to the body, the method further comprising removing the pull-through tip from the body and utilizing the pull-through tip to pull the retained portion of the implantable lead extension through the subcutaneous tunnel.

22. The method of claim 21, wherein the body is a sheet having cut-outs with the implantable lead extension being positioned about the cut-outs.

23. The method of claim 22, wherein removing from the body the portion of the implantable medical lead extension having the length that is adequate to extend through the subcutaneous tunnel present in the patient such that the implantable medical lead extension is in the partially removed configuration on the body comprises removing the portion with the length substantially equal to one circumference of the configuration.

24. The method of claim 15, wherein the body is H-shaped with the implantable lead extension being positioned about a center of the H-shape.

25. The method of claim 15, wherein the body is a disc with a circumferential groove and wherein the implantable lead extension is positioned within the groove about the disc.

26. A method of implanting an implantable lead extension, comprising:
providing a kit comprising a body and the implantable medical lead extension attached to the body, the implantable medical lead extension including a proximal connector and a distal connector;
introducing the kit into a sterile field where a patient is located;
removing from the body at least a portion of the medical lead extension; and
positioning the portion of the implantable medical lead extension within a subcutaneous tunnel within the patient.

27. The method of claim 26, further comprising attaching the kit to a surgical drape within the sterile field.

28. An implantable medical lead extension, comprising:
an elongated portion containing electrical conductors;
a distal end connector on a distal end of the elongated portion, the distal end connector having a bore for receiving a proximal end of an implantable medical lead, the bore containing electrical connectors that are connected to corresponding electrical conductors from the elongated portion; and
a proximal end connector on a proximal end of the elongated portion, the proximal end connector having a main body with a pluggable physical connection framework for connecting to a stimulation device, the proximal end connector having electrical connectors that are connected to corresponding electrical conductors from the elongated portion.

29. The implantable medical lead extension of claim 28, wherein the electrical conductors are oriented perpendicularly from the longitudinal direction of elongation of the elongated portion.

30. A kit, comprising:
a body having features; and
an implantable medical lead extension attached to the body in a configuration defined by the features of the body, with the implantable medical lead extension in the configuration including a distal end connector having a bore for receiving a proximal end of an implantable medical lead and a proximal end connector having a main body with a pluggable physical connection framework for connecting to a stimulation device, wherein the body is a sheet and the features comprise a plurality of cut-outs, the implantable medical lead extension being passed through the cut-outs to form the configuration.

31. A kit, comprising:
a body having features; and
an implantable medical lead extension attached to the body in a configuration defined by the features of the body, with the implantable medical lead extension in the configuration including a distal end connector having a bore for receiving a proximal end of an implantable medical lead and a proximal end connector having a main body with a pluggable physical connection framework for connecting to a stimulation device, wherein the features are positioned on the sheet such that a circumference of the configuration corresponds to a length of the implantable medical lead extension needed for tunneling to a lead connection site from an entry site.

32. A kit, comprising:
a body having features; and
an implantable medical lead extension attached to the body in a configuration defined by the features of the body, with the implantable medical lead extension in the configuration including a distal end connector having a bore for receiving a proximal end of an implantable medical lead and a proximal end connector having a main body with a pluggable physical connection framework for connecting to a stimulation device, wherein the features of the body create an H-shape with the implantable medical lead being wrapped about a central portion of the H-shaped body.

33. A kit, comprising:
a body having features; and
an implantable medical lead extension attached to the body in a configuration defined by the features of the body, with the implantable medical lead extension in the configuration including a distal end connector having a bore for receiving a proximal end of an implantable medical lead and a proximal end connector having a main body with a pluggable physical connection framework for connecting to a stimulation device, wherein the body comprises a disc and wherein the features provide an outer groove about a circumference of the disc and wherein the implantable medical lead extension is positioned about the groove.

* * * * *